United States Patent [19]

Burk

[11] Patent Number: 5,082,529
[45] Date of Patent: Jan. 21, 1992

[54] COLOR MEASUREMENT AND CONTROL OF A SHEET MATERIAL

[75] Inventor: Gary N. Burk, Powell, Ohio

[73] Assignee: ABB Process Automation Inc., Columbus, Ohio

[21] Appl. No.: 499,012

[22] Filed: Mar. 27, 1990

[51] Int. Cl.$^5$ .............................. D21F 11/00
[52] U.S. Cl. .................. 162/198; 162/DIG. 11; 8/400; 364/471; 356/405; 356/425; 356/429
[58] Field of Search ............... 162/198, 263, DIG. 10, 162/DIG. 11; 8/400; 356/405, 406, 407, 429, 416, 418, 419, 425; 364/470, 471

[56] References Cited

U.S. PATENT DOCUMENTS

| | | | |
|---|---|---|---|
| 3,936,189 | 2/1976 | De Remigis | 356/405 |
| 3,992,100 | 11/1976 | Lodzinski et al. | 162/263 |
| 4,019,819 | 4/1977 | Lodzinski | 162/263 |
| 4,098,641 | 4/1978 | Casey et al. | 162/198 |
| 4,439,038 | 3/1984 | Mactagart | 356/419 |

OTHER PUBLICATIONS

Machamer, "Major Break-through in Reliable On-Line Control of Opacity", Paper Trade Journal, Apr. 29, 1974, pp. 20-24.

Quinn, "Automatic Colour Control on the Papermachine", Paper Technology, vol. 9, No. 4, 1968, pp. 317-320.

Christie, "On-Machine Measurement of the Chromatic Aspects of Appearance", TAPPI, vol. 60, No. 2, Feb. 1977, pp. 119-121.

Primary Examiner—Karen M. Hastings
Assistant Examiner—Todd J. Burns
Attorney, Agent, or Firm—Chilton, Alix & Van Kirk

[57] ABSTRACT

The stack reflectance is predicted from an on-line, wavelength dependent measurement of the sheet reflectance and the on-line measurement of the sheet opacity at a wavelength interval. The stack reflectance Rst is then used to predict and/or control stack color, preferably by using the parameter $K/S = (1 - Rst^2)/2 \, Rst$ where K is the dye absorption coefficient and S is the dye scattering coefficient.

15 Claims, 2 Drawing Sheets

COLOR MEASUREMENT

58 At 32 Read from 28, 30
- R ref (w) on 46
- I (w) 48
- S (w) 50
- $V_1, V_2$ 52, 54
- Rwht (w) 42
- OP (w) 44

↓

60 Determine Rblk (w) using Eq. 7

↓

62 Determine Rst (w) using Eq. 4 and 5

↓

64 Determine Cst (w) using Eq. 2

↓

66 Display Color at 56

Fig. 2A

COLOR CONTROL

70 At 22 Select Color Target Ct

↓

72 Compare Color Target Ct with Measured Color Cst(w)

↓

74 Match Ct with Cst (w) by varing colorants at 26

Fig. 2B

COLOR MEASUREMENT AND CONTROL OF A SHEET MATERIAL

BACKGROUND OF THE INVENTION

The present invention relates to color measurements, and in particular, to the measurement and control of the color of low opacity sheet material during production.

Color in sheet materials of opacity less than 100%, such as paper, is often defined to be the color of a sufficient number of layers of that material such that the removal of a single layer does not change the color. On-line color measurement during the manufacture of these materials for the purpose of production control is, by necessity, performed on the single layer being made. The color at this point is different from that of the stack of material because of the low opacity, i.e., part of the source illumination passes through the sheet and is either lost or reflected by a material of different color. To reduce or eliminate this difference in color, the sheet being measured is often backed with a reflecting surface. If this surface has the same color as the sheet being manufactured and the interface between the sheet and reflector causes no optical perturbation, the measured color will be the same as that of the stack. This is because the backing reflector replaces the stack and is optically identical to it.

In practice, this is a difficult measurement condition to achieve because the color of the reflector is rarely the same color as the sheet, and because the transparent interface between the sheet and reflector is difficult to maintain. When the color of the reflector differs from that of the sheet, the usual condition, the color of the sheet will differ from that of an infinite stack by an amount that is a function of the difference in color between the sheet and the reflector and also of the opacity of the sheet. The difference in color is not a serious problem for sheets of constant opacity because the error it produces will be constant. Therefore, process control information can still be obtained by measuring the color of the sheet backed by the deviant reflector when an infinite stack of sheets is at the proper color. Though this measurement will be different from that of the infinite stack, controlling the process to produce this single sheet color will also produce the correct stack color.

If the opacity of the sheet varies, a difficulty arises because the fraction of the reflected energy from the backing reflector will vary and, as this reflector is a different color from the sheet, the total measured energy from the sheet will vary, i.e., the measured color will vary as a function of opacity. If process control is effected based on this measurement, the controller will attempt to produce a single sheet of the new opacity whose color is the same as the original target. A stack of this material will not have the same color as a stack of the original material.

Color can be defined as a three dimensional unit representing the response of the CIE Standard Observer to any spectral radiant energy distribution. This empirical triad of sensitivities has been constructed to simulate the perceptual response of an average human observer. As applied to reflecting objects, color can be calculated by measuring the reflectance at each wavelength and integrating the product of this reflectance, the illuminance of interest, and the Standard Observer sensitivity over the visual spectrum.

Colorant is a material added to a sheet for the purpose of adjusting its triad $a^*$ and/or $b^*$ values. This will usually also reduce its $L^*$ value. However, this is not the primary purpose. A material (such as carbon black) that adjusts $L^*$ only without an affect on chromaticity is considered an opacifier.

The color "white" can be roughly defined as that color measured in response to a spectral energy distribution of uniform intensity. More precisely, white is any color whose CIE tristimulus triad is $L^*$=any number greater than 0, $a^*=0$, and $b^*=0$ where $a^*$ represents the red-green axis, $b^*$ represents the yellow-blue axis, and $L^*$ represents the lightness or overall reflectivity of the material relative to a reference material such as freshly prepared Barium Sulfate. Because human color perception has low sensitivity at several spectral areas, for example at 400–410 nm, deviations from a "flat" spectrum at those points has little effect on color. Further, a wide range of colors with small $a^*$ and $b^*$ values is commonly referred to as white. For the application of the present invention, an $a^*$ or $b^*$ value of $+/-5.0$ may be considered to be white. Exceeding this range will result in a gradual degradation of its usefulness.

The term "opacity" as used here refers to the ratio of the reflectance of a sheet with no reflecting background (black) to the reflectance of that sheet with a reflecting background. The TAPPI specification calls for a background of 89% reflectance.

The term "stack" is used here to mean a sufficient number of layers of a sheet material such that removal of one layer does not affect the reflectance factor of the surface layer. This is often called an infinite stack.

SUMMARY OF THE INVENTION

The fundamental premise underlying the present invention is that when the opacity of a near white sheet varies due to either a variation in processing conditions or the variation of a non-colorant component, this variation takes place at all wavelengths to approximately the same magnitude.

Therefore, if the sheet opacity is measured at any spectral area, for example the 560 nm centrum defined in TAPPI T-425, this measurement will be approximately true for the entire visible spectrum. This approximation loses accuracy as the difference between the wavelength of interest and the opacity measurement central wavelength increases. However, within the visible spectrum, this error will be small. Further, when used for the determination of color, the results of the error will be smaller yet because of the low sensitivity of each visual spectral limit on color, i.e., there is little color perception at either 400 nm or 700 nm.

If, at a given wavelength, the opacity, the reflectance of a sheet over a reflector, and the reflectance of the reflector are known, the reflectance of that sheet when backed by a stack of the same material can be determined from intermediate computations using readily available variables. In particular if the opacity, the sheet reflectance over a white background, and the reflectance of the white background are known or measured, the reflectance of that sheet without a background may be determined. This enables the solution of well known equations for the color of an infinite stack of sheets.

In one possible configuration, a spectrophotometric reflectance sensor, such as is commercially available from ABB/Process Automation Business, Inc., Columbus, Ohio, under the trademark AccuRay Color/Brightness sensor, is used to measure the reflectance of a sheet being produced, such as a sheet of low opacity, near white paper. At approximately the same point in the production process, an opacity sensor, such as is commercially available from the same source under the trademark AccuRay Optipak, is used to measure the opacity of the sheet, e.g., the TAPPI opacity. The sheet measured by the reflectance sensor is backed by a white reflector, whose average reflectance could be any value but, most conveniently, is the same value as the TAPPI opacity standard, 89%. The measurement of the reflectance sensor is used to calculate the color of the sheet.

A color control system can use this measurement to produce a target color of paper. This target is selected such that the color of a stack of this paper will be as desired, although the color of the single sheet being measured will be different. When, due to non-colorant related changes in the process, the opacity of the sheet varies, the difference between the single sheet color and the color of a stack also varies. The opacity sensor measures this variation. The change in opacity is used to calculate a new target set of measured variables. The control then produces this new single sheet color which, when measured in the stack condition, will match the target stack color. The reflectance sensor measurement can optionally be adjusted to display the final reflectance of the stack to the operator.

The present invention can be easily applied to non-uniform changes in opacity, such as those caused by colorants, if the spectral absorption effects of the colorant are known and accordingly compensated. Further, in a production context where the colorant change is being forced by an automatic control system, the known colorant absorption spectrum allows the prediction of the opacity change before the color change is actually affected, and therefore, compensatory action by the control system can be implemented in feed forward, rather than feed back mode.

BRIEF DESCRIPTION OF THE DRAWINGS

FIG. 2 is a high level flow chart representing the method steps associated with the invention as implemented in the system represented by FIG. 1.

DESCRIPTION OF THE PREFERRED ENVIRONMENT

Figure 1:
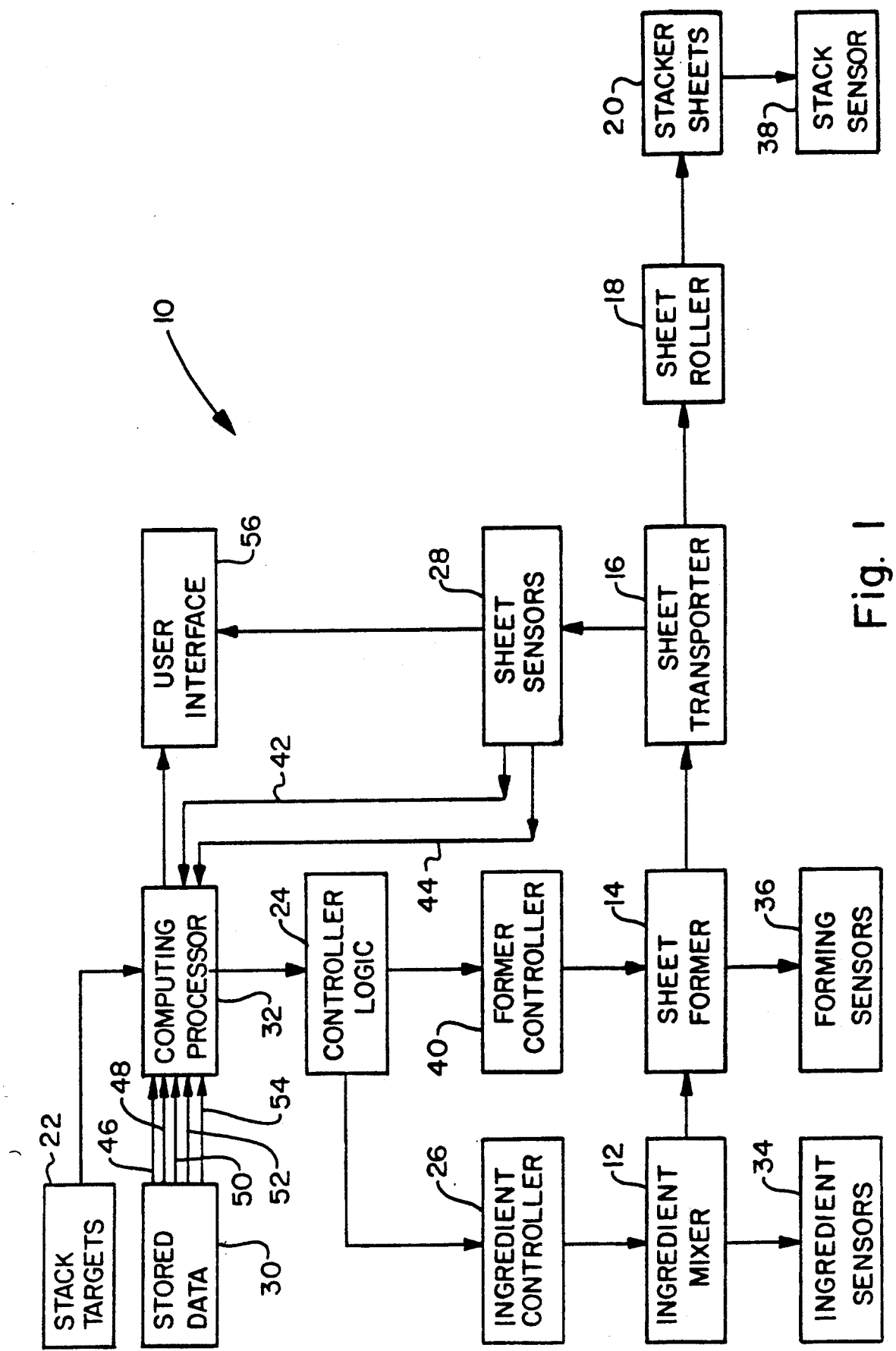
FIG. 1 is a block diagram representing selected process components or stages associated with the production of low opacity sheet material and the measurements and control system in accordance with the invention.

FIG. 1 schematically represents a sheet forming system 10 in accordance with the invention such as would be employed for the production of paper. Block 12 represents the introduction of the physical ingredients used in the sheet production process, such as fibers or the like forming the basic matrix of the paper, binders and the like to hold the fibers together, colorant, opacifiers and other ingredients such as catalysts, drying enhancers, and the like, all of which are familiar to and commonly used by the paper making industry. These ingredients are fed in measured quantities into a sheet forming machine 14 of any conventional type, the output of which is typically a continuous sheet of material that is transported through a system of tension rollers and the like represented in block 16, until the sheet material is in a condition suitable for being rolled unto reels, as represented in block 18. Ultimately, the paper on the rolls is cut and furnished to the end user, in the form of stacked sheets represented at 20.

As discussed in the background portion of this specification, the color of low opacity, near white sheet material is usually specified in terms of an infinite stack of sheet, i.e., the sheet material as rolled on a reel at block 18, or stacked in individual sheets as represented in block 20. During the production of the sheet material, however, as represented in blocks 12, 14, and 16, any measurement of color will be different from the color of the roll or stacked sheets represented in blocks 18 and 20. In accordance with the most straight forward embodiment of the invention, a method and apparatus are described for predicting the color that a particular sheet of material passing through the sheet transport equipment 16 will have, when rolled or stacked with similar sheet materials such as 18 or 20. This color prediction is accomplished in data processing equipment represented by block 32.

In another embodiment of the invention a preselected, target color for a stack of sheets is specified by the operator in, for example, block 22. This target is compared with the real time determination of the predicted stack sheet color in functional block 32, and a signal commensurate with the color difference is delivered to a control system represented in functional block 24, which can adjust the sheet forming process 14, or change the target ingredient mix as represented in functional block 26. Under this controlled scheme, the differences between the target color established in block 22 and the predicted color of the sheets in production as determined in block 32, are fed back through the control system 24 to adjust the ingredient mix or sheet forming in functional blocks 12 and 14.

In a further refinement of the invention, a change initiated in the ingredient target mix as represented in block 26, can be fed forward into block 32 where the change in color resulting from the ingredient change is determined. A signal indicative of the predicted color changes is delivered to the control system which can adjust other ingredients or the sheet forming process to assure that the system will quickly compensate and produce sheet material at block 16 that exhibits the desired stack sheet color associated with the desired change in ingredients.

Optionally, the weight or volume of ingredients actually entering the process, the various sheet forming properties, and the color of stacked or roller sheet, can be measured as represented in blocks 34, 36 and 38, respectively.

In all embodiments of the invention, two characteristics of the sheet material are continually measured, as represented in block 28. The first property is the reflectance of the sheet backed by a white reflector whose average reflectance could be any value, but is preferably the same value as the TAPPI opacity standard 89%. A spectrophotometric reflectance sensor such as the AccuRay color/brightness sensor can be used for this purpose. The reflectance is measured as a functional wavelength, resulting from the illumination of the sheet by an illumination source I(w) of a known or measured wavelength spectrum. The reflectance of the sheet with a reflecting backing, Rwht(w), is delivered on line 42 from measurement block 28 to processing block 32.

The other measured sheet property is opacity, which is measured at approximately the same point in the sheet transport process 16 as the reflectance Rwht(w). The sensor available under the trademark AccuRay Optipak can be used to measure opacity preferably in conformance with TAPPI standards. Although the opacity of an object is generally a function of illumination wavelength spectrum, a key assumption underlining the present invention is that the opacity of the near white sheet due to either a variation in the processing conditions represented by the sheet forming in block 14, or the variation of a non-colorant ingredient in the mix represented by block 12, takes place at all wavelength to approximately the same magnitude. Therefore, if the sheet opacity is measured at a given spectrum interval, for example the 560 nm spectrum defined in TAPPI T/425, this measurement will be approximately true for the entire visible spectrum. Thus, the opacity measurement performed in block 28 is assumed to be independent of wavelength. The signal delivered from block 28 on line 42 to the processing block 32, is represented by OP($\underline{w}$), indicating that although opacity is a variable, the variation is measured only at a given wavelength range and the magnitude of the opacity change at every other visible wavelength is assumed to be the same as the change in the measured opacity.

The system in accordance with the present invention further includes a stored data based represented at block 30, which contains functional, tabular, or similar wavelength dependent representation of the reflectance Rref(w) of the backing reflector used for the measurement of Rwht(w) as represented in functional block 16; the illumination intensity I(w) of the source used to perform the reflectance measurements at block 16; and the Standard Observer Sensitivity to reflected light, S(w); and the values of the wavelength maxima and minima to which the human eye is sensitive, V1, V2. Each of these types of stored data are delivered over lines 46, 48, 50, 52, and 54 to the processor 32. In the most straightforward embodiment of the invention, the resulting color of the infinite stack of sheets corresponding to the particular sheet being transported in the production process as represented at block 16, is determined and can be displayed to the operator or recorded, via an output device 56, such as a monitor, printer, ink pen, or the like.

In connection with the following detailed description of how this color prediction is accomplished in accordance with the invention, the reader's attention is directed to the Appendix which contains certain quantitative relationships that underly the apparatus and method of the present invention. In the Appendix, Equation 1 represents a generalized formulation of a "color operator" C(w) for determining the color of a reflecting object, by measuring the reflectance at each wavelength R(w) and integrating the product of this reflectance, the illumination of interest, I(w) and the standard observer sensitivities, S(w), over the visual spectrum from wavelength v1 to wavelength v2. The color of a stack of reflecting sheets, Cst(w), has a similar integral formulation, wherein the reflectance of the stack as a function of wavelength, Rst(w) is used, as represented in Equation 2. In a similar manner the color of a single sheet, Csh(w) can be determined if the appropriate reflectance function Rsh(w) is used in the integral formulation represented by Equation 3.

Equations 1, 2 and 3 in the Appendix represent vectors, wherein C(w) indicates the results of applying the "color operator" to each of the triad of Standard Observer sensitivity curves Sz(w), Sy(w) and Sx(w). The integration over the visual wavelength domain of each of these sensitivity curves with the reflectance curve of the object being measured and also with the energy curve of the illuminant results in three scalar values which, taken together, form the three dimensional color vector. The CIE Tri-stimulus Standard Observer is represented by the three curves S(w) called "z", "y", and "x". The results of integrating these curves with the object's reflectance curve and the illuminant energy curve are called "Z", "Y", and "X". This triad of Z,Y,X is the CIE color vector. Inconveniently, Z,Y,X color is nonlinear and, for additional reasons, seldom used. Instead, there are numerous algebraic transforms into other triads that are more convenient for particular applications. CIE L*, a*, b* is one of these triads, Hunter L, a, b, is another. All such systems of units commonly in use today are based on transforms from the CIE Z,Y,X units.

It should be appreciated that the reflectance of an object is dependent on a number of variables, including the particular colorant make up and the sheet opacity. A major contributor to the difference in color perceived when viewing a single sheet of low opacity material, and a stack of the same low opacity material, is the higher opacity resulting from the stacking of the sheets. It should be evident, however, that while a given portion of sheet material is being transported as represented in block 16 of FIG. 1, a stack of the same sheet material is not available for obtaining a reflectance measurement equivalent to $R_{st}$, so that the stack color can not be predicted by using Equation 2 directly.

Practitioners in this field of technology are familiar with an expression by which the reflectance of a stack of sheets can be expressed in terms of the reflectances of a single sheet, as set forth in Equations 4 and 5 of the Appendix. The parameter a is expressed in terms of two reflectances which are relatively easily determined, Rwht and Rref, as, for example, measured or stored in block 28 or 30 in FIG. 1. The reflectance Rblk, however, can not normally be measured in a production environment such as represented by blocks 12, 14, and 16 in FIG. 1, since it is difficult to arrange a black cavity behind the sheet as it is transported.

In accordance with the invention, it is assumed that the wavelength dependent value of Rblk, is equal to the wavelength independent, measured opacity OP($\underline{w}$) multiplied by the wavelength dependent reflectance of the sheet with backing reflector, Rwht(w). Equation 6 of the Appendix shows this relationship in its general form and Equation 7 shows this relationship in the most convenient form for use with the present invention. If a TAPPI sensor is used for the opacity measurement (yielding a single value), Equation 7 is used. If an actual wavelength dependent opacity measurement is made, Equation 6 is used. (The use of Equation 6 is redundant because an on-line wavelength dependent opacity measurement would include the measurement of $R_{blk}$ directly, so that if the raw measurement data were available, no calculation would be required.) All variables for determining parameter a in Equation 4 are thus either measurable or available as stored data, in the blocks 28, 30 of FIG. 1.

The significant advantage flowing from the assumption regarding the opacity, is achieved because the only required wavelength-dependent measurement, is for Rwht. The other wavelength dependent functions I(w), S(w) are stored values. This significantly reduces the complexity of the integration of the data acquisition and computations to be performed in blocks 28 and 32. It also reduces the measurements required and the complexity of the hardware.

FIG. 2 shows the method steps associated with implementing the straightforward embodiment of the invention, whereby the color function is determined in block 32 and the resulting indicia of color are displayed in blocks 56 of FIG. 1. In block 58, the values of Rref(w), I(w), S(w), V1, and V2 are obtained from block 30 of FIG. 1 via lines 46, 48, 50, 52, and 52, respectively. From block 28 in FIG. 1, the measured data representing Rwht(w) and OP(w), are obtained via lines 42 and 44. These data are combined at appropriate intervals of wavelength in functional block 60, to calculate the wavelength dependent value of Rblk as defined in Equation 7.

Next, as represented in block 62, the wavelength dependent values of Rst(w) are computed in accordance with Equations 4 and 5. At this point, measurements of the reflectance values over a number of wavelength intervals of an online single thickness of the web, have resulted in the calculation of reflectance values of a stack of that material.

Then the color function Cst, representing the color of the stack of sheet based on the single sheet as measured during the sheet transport in block 16, is computed in functional block 64 according to Equation 2. This color operator implies that the integral (actually a summation) is performed three times, once for each of the CIE Tri-Stimulus sensitivity curves. The result of these summations is CIE color units Z,Y,X. Although not required, the CIE units may be connected into another color scale by using the appropriate transform. The calculated color is then compared to the target color and errors are determined. The processor 32 then generates a signal 66 in functional block 68 which is delivered on line to block 56, where it is displayed, recorded, or the like.

Although one may convert from spectral reflectances to color, the inverse conversion is not possible, i.e., a three variable vector may not be uniquely transformed into a vector of more than three dimensions, such as a 16 or 32 point reflectance curve. Thus, there are many different reflection spectra that evaluate to the same color. This leads to the phenomenon called "Metamerism" in which two objects matches by one illuminant do not match by another.

In the second embodiment of the invention, a target stack color is established, and the color control system takes corrective action in order to maintain the color of the single sheet during production such that when the sheets are stacked, the target stack color is achieved. When, due to non-colorant related changes in the process, i.e., changes in the matrix, binder opacifier, or other ingredients introduced into the process at blocks 12 or 14 in FIG. 1, the opacity of the sheets varies, the difference between the single sheet color and the color of the stack will also vary. The opacity sensor measures this variation and the change in opacity is used in conjunction with the target set of Rst from the Equation 2, to calculate a new target set of Rwht, according to Equations 7 and 8 (which is derived from Equation 5).

This procedure is summarized in blocks 70-74 of FIG. 2. In block 70, a quantitative expression or relationship for color target Cst is formed based, for example, on the target selected by the operator via block 22 of FIG. 1. A target set of Rst would be inferred (which can be predetermined and stored in block 22 of FIG. 1, if the functional forms of I(w) and S(w) are known a-priori and stored in block 30 of FIG. 1).

Color in paper is most often controlled by the variation of colorants called dyes. A dye is a material that attaches to the paper fibers and other components and acts to absorb light of different wavelengths in a non-uniform fashion. For example, a red dye will absorb blue and green light more than red light (400–600 nm more than 600–700 nm). Thus, the variation of the concentration of a dye in the paper will affect its reflective curve so as to change its color. Because all non-fluorescent dyes absorb light, the paper will always become darker (the "L" color dimension will be reduced in value) when dye is added. The effect on the "a" dimension (red-green axis) and the "b" dimension (yellow-blue axis) will depend on the type of dye. When a color error is measured, the controller may calculate a variation in the dye concentration that will result in a color change equal to the magnitude of the error if it knows the absorption characteristics of the dye or dyes in questions. The controller will then instruct the dye addition actuator to make that change.

Normally, there will be at least three dyes available and the controller must know the characteristics of each. The controller can, for example, use a least square error method to calculate the three dye combination that will come closest to eliminating the color error. In practice, it is best to define the dyes' characteristics as a wavelength array of the rate of change of K/S vs. concentration (K=absorption coefficient, S=scattering coefficient), because K/S is linear with concentration whereas absorption is not. K/S may be calculated from knowledge of the reflectance (at each wavelength) of an infinite stack.

This is the basis for another embodiment of the present invention, the accurate determination of K/S values. K/S values are used in many color control schemes applied to paper, plastics, textiles, and homogeneous, scattering materials. The K/S values are calculated from reflectance measurement through the relation, $$\frac{K}{S} = (1 - R^2)/2R$$

where R represents the reflectance of an infinite stack, i.e., Rst(w).

Conventionally, the measurement of R is made on-line, so that the calculated K/S is correct only if the opacity of the single sheet is 100. This is usually not true, i.e., the calculated K/S values are usually wrong. Present controllers deal with this my making repeated measure-control cycles. If the error in K/S is not excessive, the system will converge on the target. By using the present invention to calculate first the R values of the on-line sheet when it is measured as a stack, and then using these corrected R values to calculate the K/S array, the K/S array will be correct, and the number of measurement-control reiterations will be reduced, perhaps to one. This will save off-target production (scrap) and system realtime.

In FIG. 2B, block 74 indicates the matching of the color target to the calculated color of the stack by means of adjusting the dyes and/or other colorants. Whether such adjustment is by mathematical prediction or trial and error is dependent on the preferred techniques of the particular suppliers of paper processing equipment.

It should be appreciated that the method in accordance with the invention can be easily applied to non-uniform changes in opacity, such as those caused by colorants if the expected absorption effect of the colorant is known and accordingly compensated. This would be taken into account, for example, by using Equation 6 rather than Equation 7 in association with Equations 4, 5, and 8. The functional form 0(w) would be stored in block 30 as a known relationship, but the magnitude at each wavelength would fluctuate in accordance with non-colorant opacity changes as described previously.

APPENDIX $$Color = L^*, a^*, b^* = (Z, Y, X) = C(w)$$

$$C(w) = \int_{v1}^{v2} R(w)I(w)S(w)dw \quad \text{Eq. 1}$$

wherein S(w) is Sz(w), Sy(W) and Sx(w) sequentially $$Cst(w) = \int_{v1}^{v2} Rst(w)I(w)S(w)dw \quad \text{Eq. 2}$$

$$Csh(w) = \int_{V1}^{v2} Rsh(w)I(w)S(w)dw \quad \text{Eq. 3}$$

$$Rst(w) = a - (a^2 - 1)^{0.5} \quad \text{Eq. 4}$$

where $$a = 0.5 [Rwht + (Rblk - Rwht + Rref)/Rblk^*Rref] \quad \text{Eq. 5}$$

and
R = reflectance
Rst = reflectance of stack of sheets
Rsh = reflectance of single sheet
Rwht = % reflectance of sheet with reference reflector as background
Rblk = % reflectance of sheet with no reflector
Rref = % reflectance of background reflector
(all as function of wavelength)

$$Rblk = O(w) * Rwht(w) \quad \text{Eq. 6,}$$

where O is opacity as function of wavelength $$Rblk = OP(\underline{w}) * Rwht(w) \quad \text{Eq. 7,}$$

where OP is independent of wavelength $$Rwht = (2^*a^*(Rblk^*Rref) - (Rblk + Rref)/Rblk^* - Rref - 1) \quad \text{Eq. 8}$$

I claim:

1. A method for generating a signal commensurate with the color of a stack of near white sheet of low opacity material from measurement of the properties of a relatively thin sheet of the material, comprising the steps of:

positioning a reflector having a known wavelength-dependent reflectance Rref(w) at a first measurement location;
positioning a single sheet of the material over the reflector;
illuminating the sheet at the first measurement location with a light source having a spectrum of wavelengths;
determining the wavelength-dependent intensity distribution I(w) of the light source;
measuring the reflectance of the sheet Rwht(w) over the reflector at the first measurement location as a function of reflected wavelength;
measuring the opacity of the single sheet at a selected wavelength interval and generating a wavelength-independent opacity value OP;
computing a color function of the stack, $$Cst(w) = \int Rst(w) I(w) S(w) dw$$

by determining the effective stack reflectance Rst(w) from parameters including the wavelength dependent measurements of the reflectance of the single sheet, Rwht(w), the reflectance of the reflector, Rref(w), and the opacity value OP at said selected wavelength interval, and wherein I(w) is said determined intensity distribution and S(w) is a wavelength-dependent observer sensitivity; and
generating a signal commensurate with said color function.

2. The method of claim 1, wherein the step of computing includes integrating over the range of visible wavelengths, the product of,
a first functional representation, of the reflectance of the stack in terms of the wavelength-dependant reflectance of the sheet with reflector, the wavelength-dependent reflectance of the reflector, and said measured opacity,
a second functional representation, of the illumination spectrum, and
a third functional representation, of the wavelength-dependant sensitivity of the human eye to the illumination radiation.

3. The method of claim 1, wherein the opacity is measured at one wavelength interval approximately in the middle of the visible range of wavelengths.

4. The method of claim 2, wherein the sheet color is within the near white range defined by a CIE tristimulus triad of $L^* > 0$, $a^* = +/-5.0$, and $b^* = +/-5.0$.

5. The method of claim 1, wherein the step of computing includes integrating over the range of visible wavelengths, the product of,
a first functional representation, of the reflectance of the sheet without reflector,
a second functional representation, of the illumination spectrum,
a third functional representation, of the wavelength-dependant sensitivity of the human eye to radiation,
wherein the first functional representation consists of the product of said measured opacity and said wavelength-dependant measurement of the reflectance of the sheet with reflector.

6. A method for generating a signal commensurate with expected first and second stack colors associated with respective first and second portions of near white sheet material having low opacity, comprising the steps of:

positioning a reflector having a known wavelength-dependent reflectance Rref(w) at a measurement location;
passing the sheet portions of the material over the reflector;
illuminating the sheet portions at the measurement location with a light source having a spectrum of wavelengths;
determining the wavelength-dependent intensity distribution I(w) of the light source;
measuring the respective reflectances $R_1wht(w)$, $R_2wht(w)$ of the first and second sheet portions over the reflector at the measurement location as a function of reflected wavelength;

measuring the respective opacities $OP_1$ and $OP_2$ of the sheet portions at a selected wavelength; and computing respective values $C_1$ and $C_2$ of a stack color function having the form $$C(w) = \int R(w)I(w)S(w)\,dw)$$

for the first and second sheet portions from parameters including the wavelength dependent measurements of the reflectance of the sheet portions, $R_1wht(w)$, $R_2wht(w)$ the reflectance of the reflector, $Rref(w)$, and the opacity value OP at said selected wavelength, and wherein $I(w)$ is said determined intensity distribution and $S(w)$ is a wavelength-dependent observer sensitivity; and generating a signal commensurate with the difference in said respective values of the stack color function.

7. The method of claim 6, wherein the step of computing includes integrating over the range of visible wavelengths, the product of, a first functional representation, of the reflectance of the sheet in terms of the wavelength-dependent reflectance of the sheet with reflector, the wavelength-dependent reflectance of the reflector, and said measured opacity, a second functional representation, of the illumination spectrum, and a third functional representation, of the wavelength-dependant sensitivity of the human eye to radiation, 8. The method of claim 6, wherein the opacity is measured at one wavelength approximately in the middle of the visible range of wavelengths.

9. The method of claim 7, wherein the colors of the first and second sheet portions are both within the near white range defined by a CIE tristimulus triad of $L^* > 0$, $a^* = +/-5.0$, and $b^* = +/-5.0$.

10. The method of claim 6, wherein the step of computing includes integrating over the range of visible wavelengths, the product of, a first functional representation, of the reflectance of the sheet without reflector, a second functional representation, of the illumination spectrum, a third functional representation, of the wavelength-dependant sensitivity of the human eye to radiation, wherein the first functional representation consists of the product of said measured opacity and said wavelength-dependant measurement of the reflectance of the sheet with reflector.

11. A method for controlling the color of a single sheet of material in a sheet production process such that a stack of the produced sheet will have a preselected color, comprising the steps of:

positioning a reflector having a known reflectance at a first measurement location;

positioning said single sheet over the reflector;

illuminating the sheet at the first measurement location with a light source having a spectrum of wavelengths;

determining the wavelength-dependent intensity distribution of the light source;

measuring the reflectance of the sheet over the reflector at the first measurement location as a function of reflected wavelength;

measuring the opacity of the single sheet at a selected wavelength;

storing in a computational apparatus, a quantitative relationship by which the color of a stack of sheets depends on the measured reflectance of the sheet, and the reflectance of the reflector;

from said quantitative relationship, establishing a target value of the measured reflectance of the sheet corresponding to a reference measured opacity and the desired color of the stack of sheets; and controlling the sheet production by adjusting the reflectance of the sheet in response to deviations of the measured opacity from the reference measured opacity.

12. An improved method for controlling the color of a single sheet of material in a sheet production process such that the stack of the produced sheets will have a preselected color, wherein the process includes adjusting the concentration of at least one dye having a known relationship of the parameter K/S vs. concentration, where K is the dye absorption coefficient and S is the dye scattering coefficient, characterized by the steps of:

measuring the reflectance $Rwht(w)$ of a single sheet in production;

measuring the wavelength-independent opacity OP of said single sheet at a selected wavelength interval;

computing from said measurement of $Rwht(w)$ and $OP(w)$, the reflectance $Rst(w)$ that a multiplicity of said single sheet would have if stacked;

computing the parameter $K/S = (1-Rst^2)/2Rst$ from the computation of $Rst(w)$; and adjusting the dye concentration in response to changes in the computed parameter K/S.

13. The method of claim 12, wherein the step of measuring the reflectance $Rwht(w)$ includes, positioning a reflector having a known wavelength-dependent reflectance $Rref(w)$ at a first measurement location;

positioning a single sheet over the reflector;

illuminating the sheet at the first measurement location with a light source having a spectrum of wavelengths;

determining the wavelength-dependent intensity distribution $I(w)$ of the light source; and measuring the reflectance of the sheet over the reflector at the first measurement location as a function of reflected wavelength.

14. The method of claim 12, wherein the step of computing the reflectance Rst includes computing the relationship $$Rst(w) = a - (a^2 - 1)^{0.5}$$

where a is dependent on $Rwht(w)$ and $OP(w)$.

15. The method of claim 13, wherein the step of computing the reflectance Rst includes computing the relationship $$Rst(w) = a - (a^2 - 1)^{0.5}$$

where a is dependent on Rwht and $OP(w)$.

* * * * *

UNITED STATES PATENT AND TRADEMARK OFFICE
CERTIFICATE OF CORRECTION

PATENT NO. : 5,082,529
DATED : January 21, 1992
INVENTOR(S) : Gary N. Burk

It is certified that error appears in the above-indentified patent and that said Letters Patent is hereby corrected as shown below:

Column 9, line 52, "sheet" should read --sheets--.

Column 11, line 57, "sheet" should read --sheets--.

Column 12, line 29, change "OP" to --OP(w)--.

Column 12, line 66, change "Rwht" to --Rwht(w)--.

Signed and Sealed this

Eighteenth Day of March, 1997

Attest:

BRUCE LEHMAN

Attesting Officer

Commissioner of Patents and Trademarks